(12) United States Patent  
Sasayama

(10) Patent No.: US 11,740,396 B2  
(45) Date of Patent: *Aug. 29, 2023

(54) OPTICAL DEVICE

(71) Applicant: Asahi Kasei Microdevices Corporation, Tokyo (JP)

(72) Inventor: Kengo Sasayama, Tokyo (JP)

(73) Assignee: Asahi Kasei Microdevices Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/656,275

(22) Filed: Mar. 24, 2022

(65) Prior Publication Data

US 2022/0214482 A1  Jul. 7, 2022

Related U.S. Application Data

(63) Continuation of application No. 16/833,672, filed on Mar. 30, 2020, now Pat. No. 11,320,572.

(30) Foreign Application Priority Data

Dec. 5, 2019 (JP) .................................. 2019-220521

(51) Int. Cl.
G02B 5/28 (2006.01)
G01N 21/3504 (2014.01)
G01N 33/00 (2006.01)

(52) U.S. Cl.
CPC ......... *G02B 5/281* (2013.01); *G01N 21/3504* (2013.01); *G01N 33/0047* (2013.01); *G02B 5/285* (2013.01); *G01N 2201/062* (2013.01)

(58) Field of Classification Search
CPC .... G02B 5/281; G02B 5/285; G01N 21/3504; G01N 33/0047; G01N 2201/062
USPC ................. 356/431, 432, 419, 437, 439, 51; 250/343, 341.8, 339.11, 339.01, 338.1
See application file for complete search history.

(56) References Cited

U.S. PATENT DOCUMENTS

| 3,734,631 A | 5/1973 | Justice et al. |
| 2011/0090505 A1 | 4/2011 | Kuze et al. |
| 2012/0235038 A1 | 9/2012 | Nishikawa et al. |

(Continued)

FOREIGN PATENT DOCUMENTS

| JP | S485488 A | 1/1973 |
| JP | S60225803 A | 11/1985 |

(Continued)

*Primary Examiner* — Isiaka O Akanbi  
(74) *Attorney, Agent, or Firm* — Kenja IP Law PC

(57) ABSTRACT

An optical device comprises an optical filter having a substrate and a multilayer film, and an infrared light emitting and receiving device having a first conductive-type semiconductor layer, an active layer, and a second conductive-type semiconductor layer. The multilayer film has layers with different refractive indexes formed on at least one side of the substrate, in which first and second layers having refractive indexes of 1.2 or more and 2.5 or less, and 3.2 or more and 4.3 or less, respectively, in a wavelength range of 6 μm to 10 μm are alternately stacked. The optical filter includes a wavelength range having an average transmittance of 70% or more with a width of 50 nm or more in a wavelength range of 6 μm to 10 μm, and has a maximum transmittance of 10% or more in a wavelength range of 12.5 μm to 20 μm.

14 Claims, 11 Drawing Sheets

(56) References Cited

U.S. PATENT DOCUMENTS

| | | | | |
|---|---|---|---|---|
| 2014/0055652 A1* | 2/2014 | Hasegawa | ............... | G02B 1/113 |
| | | | | 348/294 |
| 2015/0146057 A1* | 5/2015 | Konishi | .................... | C03C 3/16 |
| | | | | 348/294 |
| 2016/0139038 A1* | 5/2016 | Oldsen | ............... | G01N 21/0303 |
| | | | | 356/454 |
| 2020/0072739 A1* | 3/2020 | Sasayama | ............... | G01N 21/61 |
| 2020/0218000 A1* | 7/2020 | Chung | .................... | G02B 5/281 |

FOREIGN PATENT DOCUMENTS

| | | | |
|---|---|---|---|
| JP | H0933431 | A | 2/1997 |
| JP | 2011027699 | A | 2/2011 |
| JP | 2016065786 | A | 4/2016 |
| JP | 2017015679 | A | 1/2017 |
| JP | 2017020901 | A | 1/2017 |
| JP | 2017143237 | A | 8/2017 |
| JP | 2018109619 | A | 7/2018 |
| WO | 2009148134 | A1 | 12/2009 |
| WO | 2010150787 | A1 | 12/2010 |

* cited by examiner

FIG. 8

| One side Material | Film thickness nm |
|---|---|
| ZnS | 814 |
| Ge | 463 |
| ZnS | 710 |
| Ge | 412 |
| ZnS | 703 |
| Ge | 453 |
| ZnS | 769 |
| Ge | 465 |
| ZnS | 817 |
| Ge | 453 |
| ZnS | 719 |
| Ge | 447 |
| ZnS | 581 |
| Ge | 372 |
| ZnS | 625 |
| Ge | 365 |
| ZnS | 590 |
| Ge | 332 |
| ZnS | 578 |
| Ge | 324 |
| ZnS | 553 |
| Ge | 325 |
| ZnS | 476 |
| Ge | 289 |
| ZnS | 473 |
| Ge | 278 |
| ZnS | 403 |
| Ge | 238 |
| ZnS | 404 |
| Ge | 245 |
| ZnS | 419 |
| Ge | 242 |
| ZnS | 373 |
| Ge | 207 |
| ZnS | 304 |
| Ge | 179 |
| ZnS | 315 |
| Ge | 183 |
| ZnS | 295 |
| Ge | 171 |
| ZnS | 293 |
| Ge | 169 |
| ZnS | 258 |
| Ge | 151 |
| ZnS | 226 |
| Ge | 126 |
| ZnS | 214 |
| Ge | 127 |
| ZnS | 221 |
| Ge | 128 |
| ZnS | 222 |
| Si substrate | |

| The other side Material | Film thickness nm |
|---|---|
| ZnS | 50 |
| Ge | 221 |
| ZnS | 735 |
| Ge | 495 |
| ZnS | 832 |
| Ge | 547 |
| ZnS | 587 |
| Ge | 498 |
| ZnS | 549 |
| Ge | 165 |
| ZnS | 229 |
| Ge | 606 |
| ZnS | 212 |
| Ge | 88 |
| ZnS | 225 |
| Ge | 89 |
| ZnS | 115 |
| Ge | 153 |
| ZnS | 458 |
| Ge | 174 |
| ZnS | 358 |
| Ge | 205 |
| ZnS | 124 |
| Ge | 242 |
| ZnS | 501 |
| Ge | 203 |
| ZnS | 210 |
| Ge | 468 |
| ZnS | 1121 |
| Ge | 939 |
| ZnS | 1141 |
| Ge | 1015 |
| ZnS | 579 |
| Ge | 968 |
| ZnS | 1119 |
| Ge | 944 |
| ZnS | 405 |
| Ge | 184 |
| Si substrate | |

OPTICAL DEVICE

CROSS-REFERENCE TO RELATED APPLICATIONS

The present application is a continuation application of U.S. patent application Ser. No. 16/833,672 filed Mar. 30, 2020, which claims priority of Japanese Patent Application No. 2019-220521 filed Dec. 5, 2019. The disclosures of the prior applications are hereby incorporated by reference herein in their entirety.

TECHNICAL FIELD

This disclosure relates to a NDIR gas sensor, an optical device, and an optical filter for a NDIR gas sensor.

BACKGROUND

A non-dispersive infrared (NDIR) gas concentration measuring device has been known as a gas concentration measuring device for measuring the concentration of a gas to be measured in the atmosphere. Different kinds of gas absorb infrared light at different wavelengths, and a non-dispersive infrared absorption gas concentration measuring device utilizes this principle and measures the concentration of a gas by detecting its absorption amount. Examples of the gas concentration measuring device utilizing this principle include a device which is obtained by combining a filter (a transmission member) that transmits infrared light limited to a wavelength at which a gas to be measured has absorption characteristics and an infrared light receiving device, and is configured to measure the concentration of the gas to be measured by measuring the absorption amount of infrared light absorbed by the gas. JP H09-33431 A (PTL 1) describes a carbon dioxide concentration measuring device utilizing this principle.

CITATION LIST

Patent Literature

PTL 1: JP H09-33431 A

SUMMARY

However, an optimum combination of an infrared light source, an infrared light emitting and receiving device and an optical filter for each gas to be detected has not been studied. In particular, the specifications of the optical filter have not been optimized so far.

It could thus be helpful to provide a NDIR gas sensor with high accuracy even using a simplified optical filter, an optical device, and an optical filter for a NDIR gas sensor.

The primary features of this disclosure are as described below.

One aspect of the NDIR gas sensor of the present disclosure includes:

an optical filter having a substrate and a multilayer film having a plurality of layers with different refractive indexes formed on at least one side of the substrate; and an infrared light emitting and receiving device having a semiconductor layer of a first conductive type, an active layer, and a semiconductor layer of a second conductive type; where the multilayer film has a structure in which a first layer and a second layer are alternately stacked, the first layer has a refractive index of 1.2 or more and 2.5 or less in a wavelength range of 6 µm to 10 µm, and the second layer has a refractive index of 3.2 or more and 4.3 or less in a wavelength range of 6 µm to 10 µm;

the active layer contains $InAs_ySb_{1-y}$ ($0.1 \le y \le 0.2$); and the optical filter includes a wavelength range having an average transmittance of 70% or more with a width of 50 nm or more in a wavelength range of 6 µm to 10 µm, and has a maximum transmittance of 10% or more in a wavelength range of 12.5 µm to 20 µm and an average transmittance of 5% or more and 60% or less in a wavelength range of 12.5 µm to 20 µm.

Another aspect of the NDIR gas sensor of the present disclosure includes:

an optical filter having a substrate and a multilayer film having a plurality of layers with different refractive indexes formed on at least one side of the substrate; and an infrared light emitting and receiving device having a semiconductor layer of a first conductive type, an active layer, and a semiconductor layer of a second conductive type; where the multilayer film has a structure in which a first layer and a second layer are alternately stacked, the first layer contains at least one selected from the group consisting of $TiO_2$ and ZnS, and the second layer contains at least one selected from the group consisting of Si and Ge;

the active layer contains $InAs_ySb_{1-y}$ ($0.1 \le y \le 0.2$); and the optical filter includes a wavelength range having an average transmittance of 70% or more with a width of 50 nm or more in a wavelength range of 6 µm to 10 µm, and has a maximum transmittance of 10% or more in a wavelength range of 12.5 µm to 20 µm and an average transmittance of 5% or more and 60% or less in a wavelength range of 12.5 µm to 20 µm.

One aspect of the optical device of the present disclosure includes:

an optical filter having a substrate and a multilayer film having a plurality of layers with different refractive indexes formed on at least one side of the substrate; and an infrared light emitting and receiving device having a semiconductor layer of a first conductive type, an active layer, and a semiconductor layer of a second conductive type; where the multilayer film has a structure in which a first layer and a second layer are alternately stacked, the first layer has a refractive index of 1.2 or more and 2.5 or less in a wavelength range of 6 µm to 10 µm, and the second layer has a refractive index of 3.2 or more and 4.3 or less in a wavelength range of 6 µm to 10 µm;

the active layer contains $InAs_ySb_{1-y}$ ($0.1 \le y \le 0.2$); and the optical filter includes a wavelength range having an average transmittance of 70% or more with a width of 50 nm or more in a wavelength range of 6 µm to 10 µm, and has a maximum transmittance of 10% or more in a wavelength range of 12.5 µm to 20 µm and an average transmittance of 5% or more and 60% or less in a wavelength range of 12.5 µm to 20 µm.

Another aspect of the optical device of the present disclosure includes:

an optical filter having a substrate and a multilayer film having a plurality of layers with different refractive indexes formed on at least one side of the substrate; and an infrared light emitting and receiving device having a semiconductor layer of a first conductive type, an active layer, and a semiconductor layer of a second conductive type; where the multilayer film has a structure in which a first layer and a second layer are alternately stacked, the first layer contains at least one selected from the group consisting of $TiO_2$ and ZnS, and the second layer contains at least one selected from the group consisting of Si and Ge;

the active layer contains $InAs_ySb_{1-y}$ ($0.1 \leq y \leq 0.2$); and the optical filter includes a wavelength range having an average transmittance of 70% or more with a width of 50 nm or more in a wavelength range of 6 μm to 10 μm, and has a maximum transmittance of 10% or more in a wavelength range of 12.5 μm to 20 μm and an average transmittance of 5% or more and 60% or less in a wavelength range of 12.5 μm to 20 μm.

One aspect of the optical filter for a NDIR gas sensor of the present disclosure is an optical filter for a NDIR gas sensor having a substrate and a multilayer film having a plurality of layers with different refractive indexes formed on at least one side of the substrate, where the multilayer film has a structure in which a first layer and a second layer are alternately stacked, the first layer has a refractive index of 1.2 or more and 2.5 or less in a wavelength range of 6 μm to 10 μm, and the second layer has a refractive index of 3.2 or more and 4.3 or less in a wavelength range of 6 μm to 10 μm; and the optical filter includes a wavelength range having an average transmittance of 70% or more with a width of 50 nm or more in a wavelength range of 6 μm to 10 μm, and has a maximum transmittance of 10% or more in a wavelength range of 12.5 μm to 20 μm and an average transmittance of 5% or more and 60% or less in a wavelength range of 12.5 μm to 20 μm.

Another aspect of the optical filter for a NDIR gas sensor of the present disclosure is an optical filter for a NDIR gas sensor having a substrate and a multilayer film having a plurality of layers with different refractive indexes formed on at least one side of the substrate, where the multilayer film has a structure in which a first layer and a second layer are alternately stacked, the first layer contains at least one selected from the group consisting of $TiO_2$ and ZnS, and the second layer contains at least one selected from the group consisting of Si and Ge; and the optical filter includes a wavelength range having an average transmittance of 70% or more with a width of 50 nm or more in a wavelength range of 6 μm to 10 μm, and has a maximum transmittance of 10% or more in a wavelength range of 12.5 μm to 20 μm and an average transmittance of 5% or more and 60% or less in a wavelength range of 12.5 μm to 20 μm.

Note that the above summary does not enumerate all the necessary features of the present disclosure. In addition, a subcombination of these features is also included in the present disclosure.

According to the present disclosure, it is possible to provide a NDIR gas sensor with high accuracy even using a simplified optical filter, an optical device, and an optical filter for a NDIR gas sensor.

BRIEF DESCRIPTION OF THE DRAWINGS

In the accompanying drawings:

FIG. 8 illustrates the stacked structure of the simplified filter of Examples 1 to 3;

DETAILED DESCRIPTION

Figure 1:
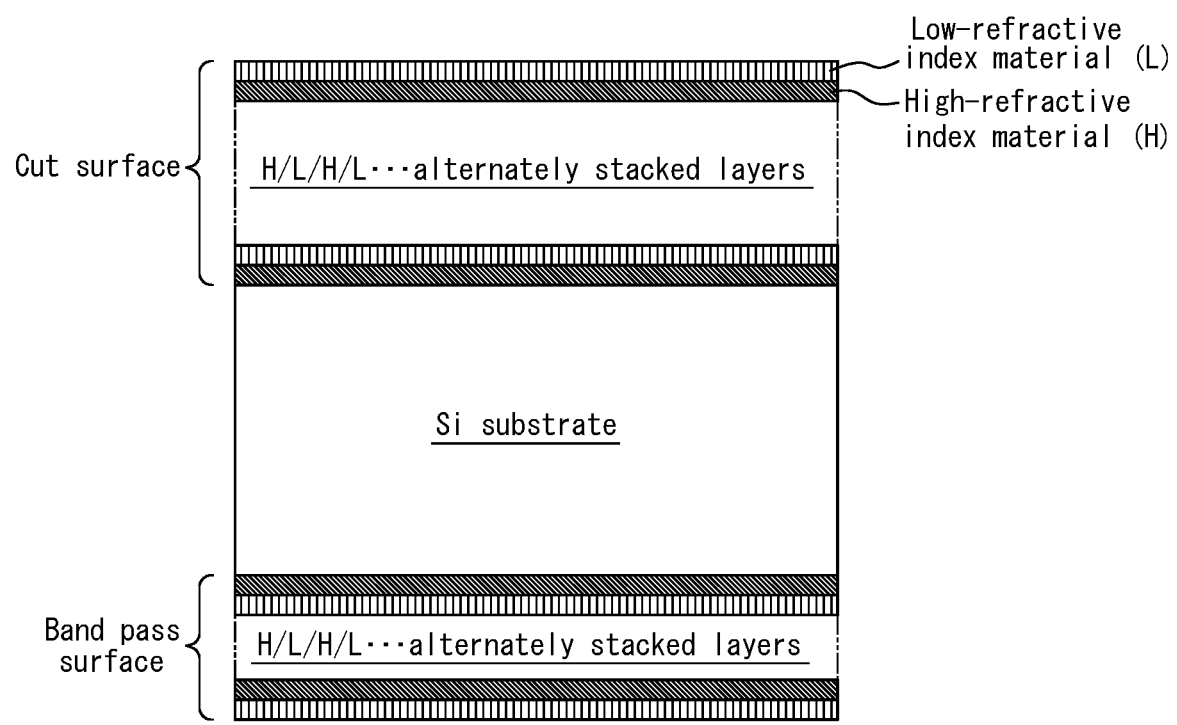
FIG. 1 illustrates an example of the cross section of the optical filter of the present embodiment.

The following describes the present disclosure based on an embodiment of the present disclosure (hereinafter, referred to as "present embodiment"). However, the scope of the claims is not limited by the following embodiment.

In addition, not all combinations of features described in the embodiment are essential to the solution to the problem.

The following describes the present embodiment with reference to the drawings. In the respective drawings described below, parts corresponding to each other are indicated by the same reference numerals, and the repetition of explanation is suitably omitted.

The present embodiment simply provides an example for realizing the technical idea of the present disclosure, and does not specify the material, shape, structure, arrangement, dimensions, or the like of each part.

The present embodiment includes all combinations of features described below.

The technical idea of the present disclosure may be variously modified without departing from the technical scope defined by the claims.

[NDIR Gas Sensor]

One aspect of the NDIR gas sensor of the present embodiment includes: an optical filter having a substrate and a multilayer film having a plurality of layers with different refractive indexes formed on at least one side of the substrate; and an infrared light emitting and receiving device having a semiconductor layer of a first conductive type, an active layer, and a semiconductor layer of a second conductive type; where the multilayer film has a structure in which a first layer and a second layer are alternately stacked, the first layer has a refractive index of 1.2 or more and 2.5 or less in a wavelength range of 6 μm to 10 μm, and the second layer has a refractive index of 3.2 or more and 4.3 or less in a wavelength range of 6 μm to 10 μm; the active layer contains InAs$_y$Sb$_{1-y}$ (0.1≤y≤0.2); and the optical filter includes a wavelength range having an average transmittance of 70% or more and 95% or less with a width of 50 nm or more and 800 nm or less in a wavelength range of 6 μm to 10 μm, and has a maximum transmittance of 10% or more in a wavelength range of 12.5 μm to 20 μm.

Another aspect of the NDIR gas sensor of the present embodiment includes: an optical filter having a substrate and a multilayer film having a plurality of layers with different refractive indexes formed on at least one side of the substrate; and an infrared light emitting and receiving device having a semiconductor layer of a first conductive type, an active layer, and a semiconductor layer of a second conductive type; where the multilayer film has a structure in which a first layer and a second layer are alternately stacked, the first layer contains at least one selected from the group consisting of TiO$_2$ and ZnS, and the second layer contains at least one selected from the group consisting of Si and Ge; the active layer contains InAs$_y$Sb$_{1-y}$ (0.1≤y≤0.2); and the optical filter includes a wavelength range having an average transmittance of 70% or more and 95% or less with a width of 50 nm or more and 800 nm or less in a wavelength range of 6 μm to 10 μm, and has a maximum transmittance of 10% or more in a wavelength range of 12.5 μm to 20 μm.

FIG. 1 illustrates an example of the cross section of the optical filter of the present embodiment.

As illustrated in FIG. 1, the optical filter of this example has a multilayer film formed by alternately stacking a layer of a low-refractive index material (L) and a layer of a high-refractive index material (H) on both sides of a Si substrate, where the low-refractive index material (L) has a refractive index of 1.2 to 2.5 in the wavelength range of 6 μm to 10 μm, the high-refractive index material (H) has a refractive index of 3.2 to 4.3 in the wavelength range of 6 μm to 10 μm, and the layer directly provided on the Si substrate is of the high-refractive index material (H). The configuration of the optical filter of the present embodiment is not limited to the one illustrated in FIG. 1. In addition, the multilayer film may be formed only on one side of the substrate, or may be formed on both sides of the substrate.

For the optical filter of the present embodiment, the multilayer film is not particularly limited as long as the first layer having a refractive index of 1.2 to 2.5 and the second layer having a refractive index of 3.2 to 4.3 are alternately stacked. However, it is preferable that the high-refractive index material (H) be directly provided on the substrate as exemplified in FIG. 1, in order to enhance the effect of the present disclosure.

In the present embodiment, the optical filter is an interference type band pass filter of the mid-infrared range. In general, an interference type band pass filter of the mid-infrared range has a large number of stacked layers, which tends to cause more defects during film formation. In addition, a large number of stacked layers in the optical filter make it difficult to miniaturize the NDIR gas sensor. Therefore, it is preferable that the number of stacked layers of the optical filter be small. However, simply reducing the number of stacked layers of the optical filter for simplification may degrade the accuracy of the gas sensor.

In order to provide a highly accurate NDIR gas sensor, it is also necessary to reduce the influence of absorption of infrared light by gases other than the gas to be detected.

As a result of examining an optimum combination of an infrared light emitting and receiving device and an optical filter, we have realized a NDIR gas sensor where the accuracy would not be degraded even using a simplified optical filter, as described below.

The simplified optical filter here limits the blocking function in a region without sensor sensitivity, thereby reducing the stacked layers of optical thin film used for blocking in this region. Using a simplified optical filter with a small number of stacked layers is expected to improve the mass productivity. In addition, reducing the number of stacked layers can reduce the defects caused during film formation, thereby improving the yield. Furthermore, warpage due to a large number of stacked layers is reduced, which suppresses the occurrence of chipping during dicing and enhances the mass production stability. The region without sensor sensitivity is determined as follows. The infrared light emitting and receiving device determines the cut-off wavelength on the long wavelength side based on the band gap energy Eg (see FIG. 13), and the details will be described later. The band gap energy Eg may be set, for example, in the range of 10 μm to 12.5 μm. In the present embodiment, the band gap energy Eg corresponds to 12.5 μm, and there is no sensitivity in a wavelength range of, for example, 12.5 μm to 20 μm. Hereinafter, the region without sensor sensitivity in the present embodiment is the wavelength range of 12.5 μm to 20 μm.

According to the NDIR gas sensor of the present embodiment, it is possible to use an inexpensive optical filter that can be easily produced while maintaining the gas detection accuracy, even in the case where the active layer of the infrared light emitting and receiving device contains InAs$_y$Sb$_{1-y}$ (0.1≤y≤0.2), and the optical filter includes a wavelength range having an average transmittance of 70% or more and 95% or less with a width of 50 nm or more and 800 nm or less in the wavelength range of 6 μm to 10 μm and has a maximum transmittance of 10% or more in the wavelength range of 12.5 μm to 20 μm.

Examples of the gas to be detected include gas species having absorption characteristics with respect to infrared light in a wavelength band of 9 μm to 10 μm such as alcohol, but are not limited thereto.

Figure 2:
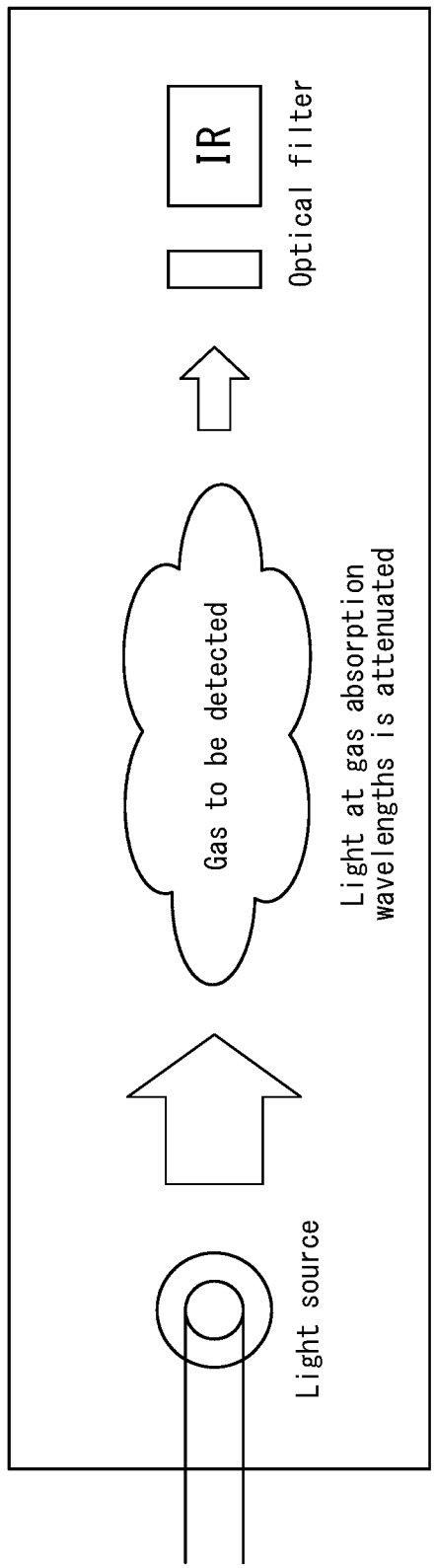
FIG. 2 illustrates an example of the NDIR gas sensor of the present embodiment.

FIG. 2 illustrates an example of the NDIR gas sensor of the present embodiment.

As illustrated in FIG. 2, in the NDIR gas sensor of the present embodiment, an infrared light receiving device is disposed in the optical path of infrared light to be emitted from an infrared light emitting device, and an optical filter for selectively transmitting the absorption wavelength of the gas to be detected is disposed in front of the infrared light receiving device.

Figure 3:
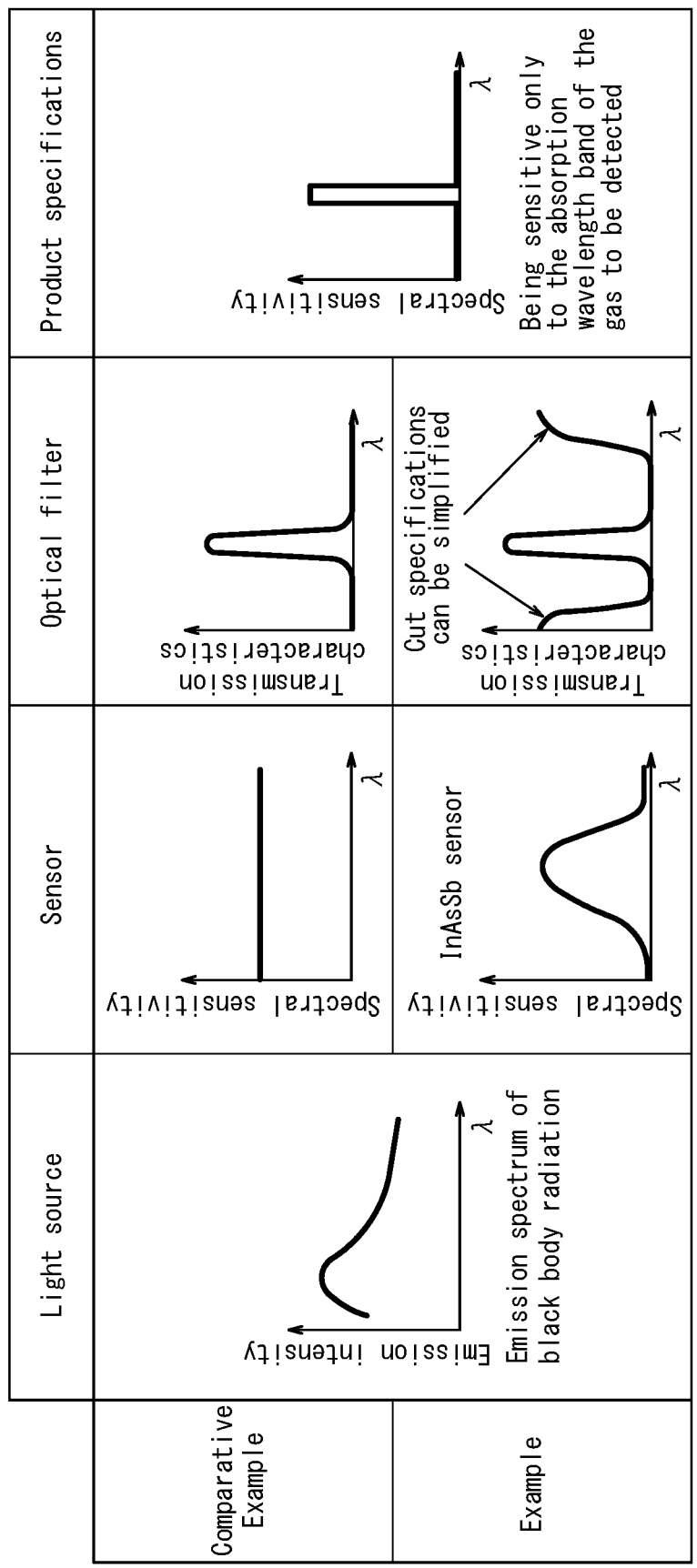
FIG. 3 illustrates and compares the optical filter of the present disclosure and the optical filter of the comparative example.

FIG. 3 illustrates and compares the optical filter of the present disclosure and an optical filter of a comparative example.

The sensor (infrared light receiving device) in the technique of the comparative example of FIG. 3 has no wavelength selectivity in spectral sensitivity (the sensitivity does not change based on wavelength). On the other hand, the present disclosure has wavelength selectivity as illustrated in FIG. 3. Therefore, in the present disclosure, the optical filter does not need to cut off the wavelength without sensitivity, which simplifies the function required for the optical filter. Although not illustrated, the same applies to the case of an infrared light emitting device having wavelength selectivity in emission intensity, where the optical filter does not need to cut off a wavelength that does not emit light, which simplifies the function required for the optical filter.

Figure 4:
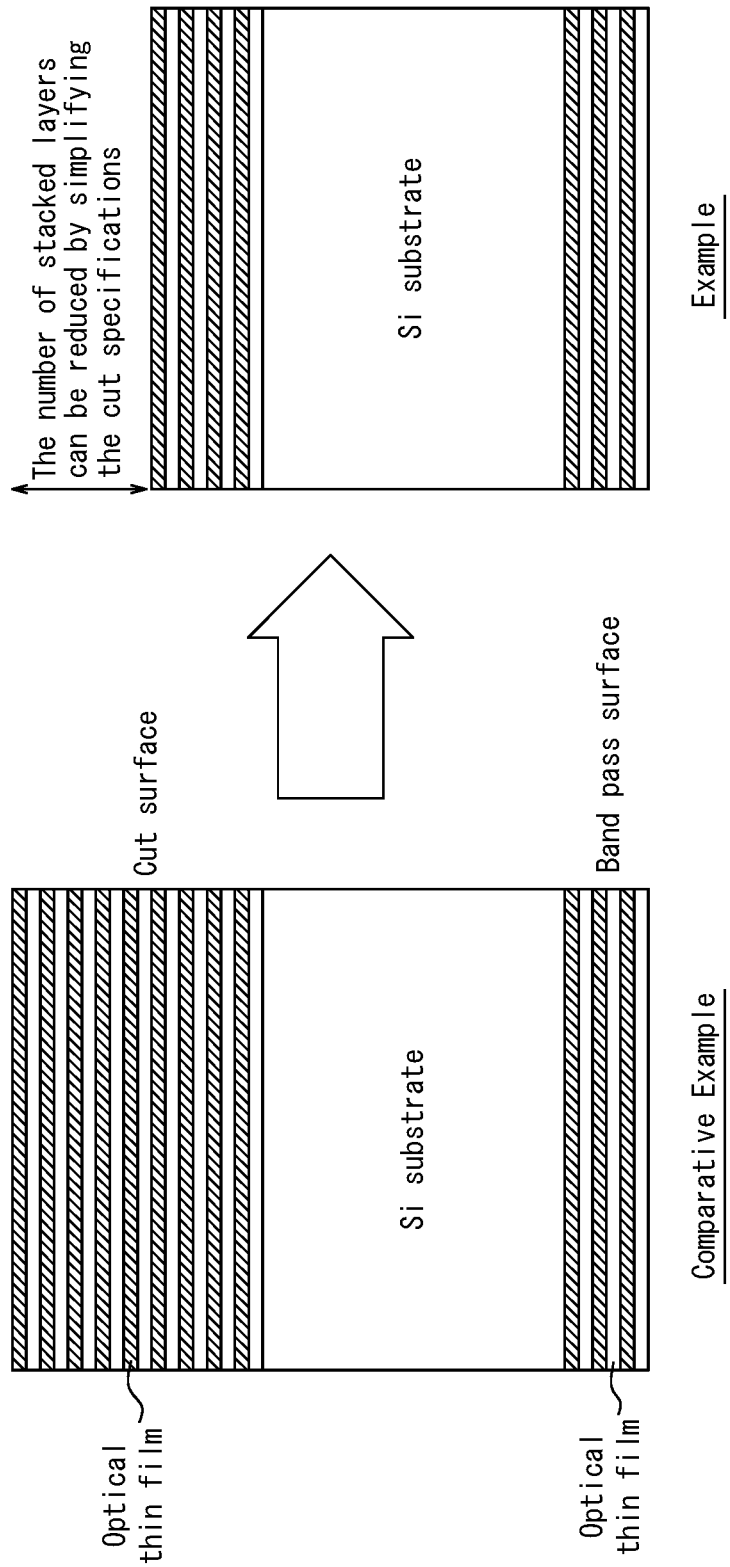
FIG. 4 illustrates the difference between the optical filter of the comparative example and the optical filter of the present disclosure.

FIG. 4 illustrates the difference between the optical filter of the comparative example and the optical filter of the present disclosure.

In the NDIR gas sensor of the present embodiment, the thickness of the film including a plurality of stacked layers can be significantly reduced as illustrated in FIG. 4, where the plurality of stacked layers is called a cut surface and determines the cut characteristics. For example, in the case of forming a multilayer film on both sides of a substrate, the ratio of the total film thickness of each side may be within the range of 0.5 to 2.0. That is, it is possible to make the film thickness of the cut surface, which is generally larger than twice the film thickness of the band pass surface, 0.5 to 2.0 times the film thickness of the band pass surface.

The following describes each component of the NDIR gas sensor of one aspect of the present disclosure.

—Optical Filter—

The optical filter has a substrate, and a multilayer film having a plurality of layers with different refractive indexes formed on the substrate. The multilayer film may be formed only on one side of the substrate, or may be formed on both sides of the substrate.

The optical filter is disposed somewhere in the optical path of infrared light emitted from the infrared light emitting device to the infrared light receiving device inside the NDIR gas sensor. The optical filter may be integrally formed with the infrared light emitting device, or may be integrally formed with the infrared light receiving device. It may be disposed in a predetermined position in the optical path. The NDIR gas sensor may include a plurality of optical filters.

The optical filter can be prepared by depositing the first layer and the second layer on the substrate by vapor deposition.

——Substrate——

Since the multilayer film is formed on one side of the substrate, the substrate may be any substrate suitable for the formation of each layer constituting the multilayer film. Examples thereof include, but are not limited to, Si substrates, Ge substrates, ZnS substrates, and sapphire substrates.

——Multilayer Film——

The multilayer film is a film having a plurality of layers with different refractive indexes, and specifically has a structure in which a first layer and a second layer are alternately stacked, the first layer has a refractive index of 1.2 or more and 2.5 or less in the wavelength range of 6 µm to 10 µm, and the second layer has a refractive index of 3.2 or more and 4.3 or less in the wavelength range of 6 µm to 10 µm.

The optical filter of the present embodiment includes a wavelength range having an average transmittance of 70% or more and 95% or less with a width of 50 nm or more and 800 nm or less in the wavelength range of 6 µm to 10 µm, and has a maximum transmittance of 10% or more in the wavelength range of 12.5 µm to 20 µm.

Note that the width of the wavelength range having an average transmittance of 70% or more and 95% or less is based on the sum total, when there are two or more such wavelength ranges.

In the optical filter of the present embodiment, the average transmittance in the wavelength range of 12.5 µm to 20 µm is preferably 5% or more and 60% or less, more preferably 10% or more and 60% or less, and still more preferably 30% or more and 60% or less. The optical filter here has the above-described cut surface and band pass surface sandwiching a Si substrate (see FIG. 1). Alternatively, it may have a multilayer film on one side of the Si substrate The upper limit of the average transmittance in the wavelength range of 12.5 µm to 20 µm is 60%, which corresponds to the upper limit of the average transmittance in the same wavelength range of the band pass surface in the present embodiment. In general, the transmittance of the band pass surface does not reach 100% even in the region without sensor sensitivity. Therefore, the average transmittance of the optical filter in the wavelength range of 12.5 µm to 20 µm has an upper limit of less than 100%, and the upper limit is determined by the average transmittance of the band pass surface. On the other hand, the lower limit of the average transmittance of the optical filter in the wavelength range of 12.5 µm to 20 µm varies depending on the average transmittance of the cut surface. That is, it is possible to change the lower limit of the average transmittance of the optical filter to, for example, 30%, 10% or 5% depending on the stacking state of the cut surface.

The reason why there is a suitable value for the average transmittance in the wavelength range of 12.5 µm to 20 µm is as follows. The number of stacked layers of the optical filter tends to depend on the width of the wavelength range to be blocked. Because there are more than one gas absorption ($CO_2$, $H_2O$, $SO_2$, $C_3H_8$, $CH_2O$, NO, etc.) in the range of 12.5 µm to 20 µm, it is necessary to block the mid-infrared light in the wavelength range of 12.5 µm to 20 µm particularly for a NDIR gas sensor so that a specific gas can be detected with high accuracy.

Figure 13:
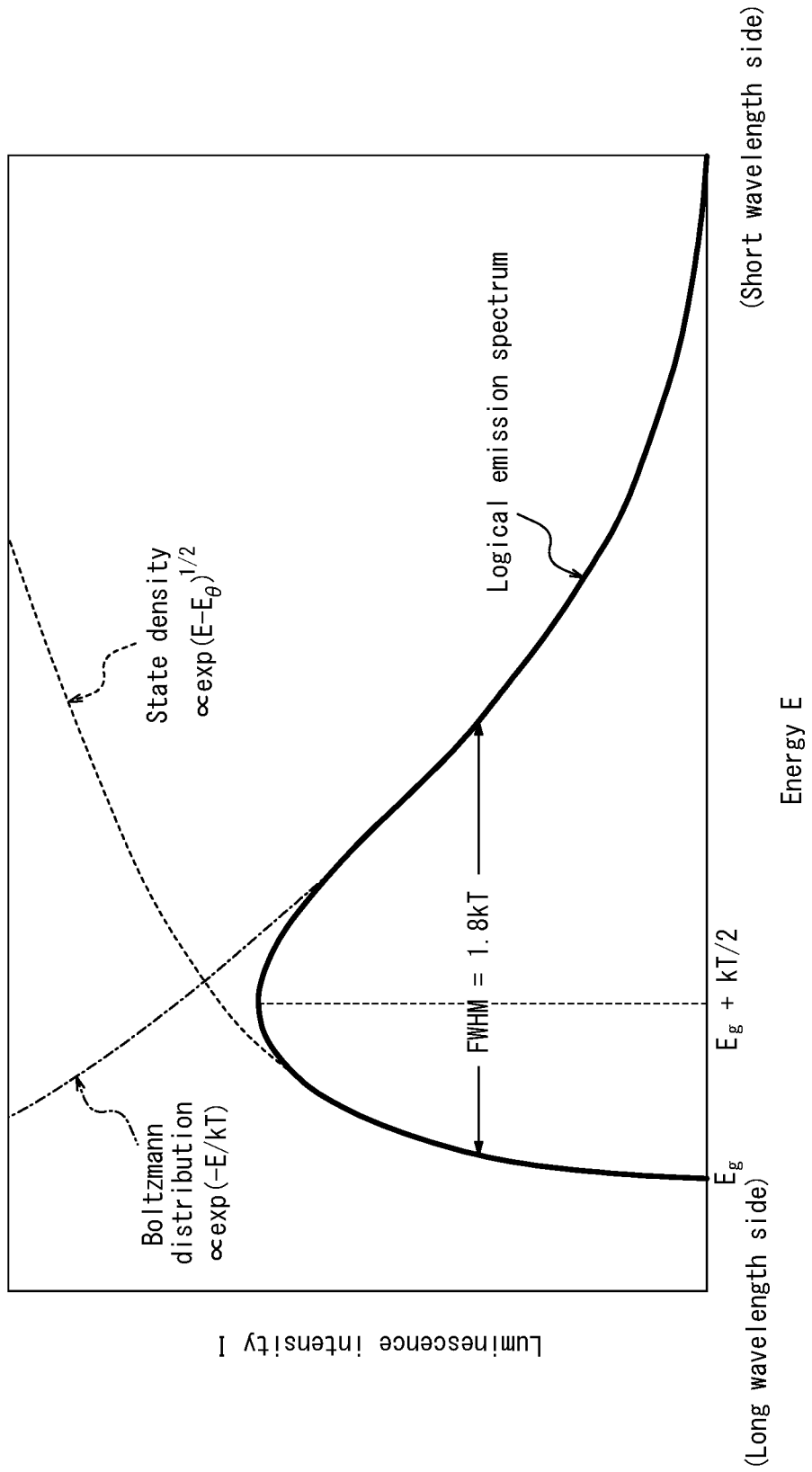
FIG. 13 illustrates the cut-off wavelength of the light emitting and receiving component.

On the other hand, the sensitivity range of the semiconductor light emitting and receiving component affects the state density and the Boltzmann distribution. FIG. 13 illustrates the cut-off wavelength of the semiconductor light emitting and receiving component. In particular, the rising wavelength of the sensitivity on the long wavelength side depends on the band gap energy Eg. The present disclosure can provide a sensor that has sensitivity in a specific absorption wavelength range according to the gas to be detected while having no sensitivity in the wavelength range of 12.5 µm to 20 µm, by optimally designing the band gap energy of the light emitting and receiving component. As a result, the blocking of 12.5 µm to 20 µm by an optical filter is no longer important, which simplifies the design of the optical filter, reduces the cost, and improves the mass productivity. In this case, the average transmittance in the wavelength range of 12.5 µm to 20 µm is more than 5%, and when the average transmittance is in the range of 5% to 60%, it is possible to simplify the optical filter while maintaining the performance as a NDIR gas sensor.

On the other hand, in order to provide a highly accurate gas sensor, it is desirable that the shape of a transmission spectrum having an average transmittance of 70% or more included in the wavelength range of 6 µm to 10 µm be close to a rectangle. In order to make the rising and falling shape of the transmission spectrum into a sharp shape that is close to a rectangular, the number of stacked layers of the optical filter is increased, and this leads to a certain blocking function even in the wavelength range of 12.5 µm to 20 µm. Therefore, the average transmittance is set within 60%. That is, the upper and lower limits in the wavelength range of 12.5 µm to 20 µm indicate a range in which the optical filter can be simplified while maintaining the performance as a NDIR gas sensor.

(Method of Measuring Average Transmittance of Optical Filter)

A method of confirming that the average transmittance of the optical filter in the wavelength range of 6 µm to 10 µm is 70% or more and 95% or less includes obtaining a transmission spectrum, for example, in a wave number range of 500 $cm^{-1}$ to 4200 $cm^{-1}$ with a wave number resolving power of 8 $cm^{-1}$ by a microscopic FT-IR apparatus (Hyperion 3000+TENSOR 27 made by Bruker), and dividing the numerical integral value of the transmittance in the above wavelength range by the wavelength range (range). The number of measurement points is 200 points per 1000 nm (one point per 5 nm). The average transmittance in the wavelength range of 12.5 μm to 20 μm can also be confirmed with the same method.

In the case of stacking more than one first layer, the material and the thickness of each first layer may be the same or different. The same applies to the second layer. The multilayer film may further include layers other than the first layer and the second layer. Even in the case where the first layer and the second layer are alternately stacked, it is possible to have a stacked structure such as a first layer→a second layer→a third layer→a first layer→a second layer. . . .

The thickness of the multilayer film is preferably 10 μm or more and 50 μm or less, more preferably 10 μm or more and 40 μm or less, and still more preferably 10 μm or more and 20 μm or less. In this way, the time for optical filter production can be shortened and the yield can be improved. The film thickness can be measured by cross sectional SEM observation.

Taking one first layer and one second layer as one repeating unit, the number of times of alternately stacking the first layer and the second layer, i.e. the number of repeating units, is preferably 10 or more and 60 or less and more preferably 10 or more and 40 or less, respectively. In this way, the time for optical filter production can be shortened and the yield can be improved.

The number of times of alternately stacking can be measured by cross sectional SEM observation.

———First Layer———

The first layer of the multilayer film of the present embodiment is a layer having a refractive index of 1.2 or more and 2.5 or less in the wavelength range of 6 μm to 10 μm.

Examples of specific materials of the first layer include $TiO_2$ and ZnS. The first layer may be made of the above materials.

———Second Layer———

The second layer of the multilayer film of the present embodiment is a layer having a refractive index of 3.2 or more and 4.3 or less in the wavelength range of 6 μm to 10 μm.

Examples of specific materials of the second layer include Si and Ge. The second layer may be made of the above materials.

(Method of Measuring Refractive Index of First Layer and Second Layer)

Note that the refractive index in the present embodiment is a value measured by an ellipsometer in accordance with JIS K7142.

—Infrared Light Emitting and Receiving Device—

The infrared light emitting and receiving device includes a semiconductor layer of a first conductive type, an active layer of $InAs_ySb_{1-y}$ ($0.1 \leq y \leq 0.2$), and a semiconductor layer of a second conductive type.

The expression "light emitting and receiving" means having at least one of light emitting function and light receiving function, and the infrared light emitting and receiving device specifically refers to an infrared light emitting diode and an infrared photodiode.

In addition, the expression "$InAs_ySb_{1-y}$ ($0.1 \leq y \leq 0.2$)" means that In, As and Sb are contained in the layer, but this expression also includes cases of containing other elements. Specifically, this expression also includes the case where a slight change is made to the composition of this layer, for example, by adding a small amount of other elements (for example, elements such as As, P, Ga, and N in not more than several percent). The term "containing" used in expressing the composition of other layers has the same meaning.

(Method of Measuring as Composition of Each Layer)

The As composition of each layer was determined as follows by Secondary Ion Mass Spectrometry (SIMS) method. A magnetic field type SIMS apparatus IMS 7f made by CAMECA was used for the measurement. In this method, compositional analysis is performed by irradiating a solid surface with beam type primary ion species, digging in the depth direction by means of sputtering phenomenon, and simultaneously detecting the generated secondary ions. The As composition here refers to the ratio of the As element to the elements contained in each layer.

Specifically, cesium ion (Cs+) was used as the primary ion species, the primary ion energy was set to 2.5 keV, and the beam incident angle was set to 67.2°. Under these conditions, MCs+(M is Al, Ga, In, As, Sb, or the like) with a small matrix effect was detected as the secondary ion species to be detected.

At this time, sputtering was carried out under the above-described conditions and up to the depth of the target layer for a predetermined period of time to analyze the composition of the target layer. The depth of the target layer can be obtained from the thickness of each layer by cross sectional TEM measurement as described later. For the sputtering time-depth conversion in SIMS analysis, sputtering rate was obtained by measuring the sputtering depth for a certain period of time under the same condition as the analysis with, for example, a stylus profilometer, and the obtained sputtering rate was used to convert the sputtering time in the sample measurement into depth to obtain the sputtering time-depth conversion.

Then, the As composition was obtained from the signal intensity of MCs+ in each layer. For example, in the case of an InAsSb layer, the As composition was obtained by: (signal intensity of AsCs+)/((signal intensity of AsCs+)+ (signal intensity of SbCs+)).

Even if each layer has a uniform composition in the depth direction, the signal intensity sometimes distributes in the depth direction due to the influence of sputtering. In this case, the signal intensity of each layer is represented by the maximum signal intensity.

Note that the quantitative value of the Al composition obtained by the analysis can be accompanied by deviation from the true value. In order to correct this deviation from the true value, a separate sample for which the lattice constant value had been obtained with the X-ray diffraction (XRD) method was prepared, and, using this sample as a standard sample with a known As composition value, SIMS analysis was performed under the conditions for measuring the As composition of each layer. In this way, the sensitivity coefficient of the Al composition with respect to the signal intensity was obtained. The As composition of each layer was obtained by multiplying the SIMS signal intensity by the sensitivity coefficient.

In this case, $InAs_ySb_{1-y}$ having a film thickness of 800 nm stacked on a GaAs substrate was used as the separate sample. For this sample, the lattice constant was obtained with the X-ray diffraction (XRD) method using an X-ray diffractometer X'Pert MPD made by Spectris Co., Ltd., as described below, to obtain the As composition y of the standard sample.

By performing 2θ-ω co scan by X-ray diffraction, the lattice constant in the direction normal to the substrate surface of the layer containing $InAs_ySb_{1-y}$ was obtained from the peak position in the 2θ-ω co scan of the plane index of the plane corresponding to the plane orientation of the substrate surface, and the As composition y was determined from the lattice constant in the normal direction using the Vegard's rule. In this case, it is assumed that there is no anisotropic distortion of the $InAs_ySb_{1-y}$ layer. The Vegard's rule is specifically represented by:

$$a_{InAsSb} = ya_{InAs} + (1-y)a_{InSb} \qquad \text{Expression (1)}$$

Where $a_{InAs}$ is the lattice constant of InAs, $a_{InSb}$ is the lattice constant of InSb, and $a_{InAsSb}$ is the lattice constant of the $InAs_ySb_{1-y}$ obtained by the above-described X-ray diffraction. In addition, 6.0585 Å is used for $a_{InAs}$, and 6.4794 Å is used for $a_{InSb}$. A sample with $0.1<y<0.15$ was used as a standard sample for SIMS measurement.

The first conductivity type and the second conductivity type may be any of n-type (including n-type impurities), i-type (including no impurities) and p-type (including p-type impurities), respectively.

The semiconductor layer of the first conductivity type, the active layer, and the semiconductor layer of the second conductivity type may be formed on a semiconductor substrate such as a GaAs substrate or a Si substrate.

In the present embodiment, each layer may be provided in an order of the substrate, the semiconductor layer of the first conductivity type, the active layer, and the semiconductor layer of the second conductivity type, or may be provided in an order of the substrate, the semiconductor layer of the second conductivity type, the active layer, and the semiconductor layer of the first conductivity type. In the present embodiment, it is preferable that the first conductivity type be n-type and the second conductivity type be p-type.

In addition, in the present embodiment, one or more barrier layers may be provided between the semiconductor layer of the first conductivity type and the active layer and/or between the active layer and the semiconductor layer of the second conductivity type, respectively.

In the present embodiment, it is preferable that an n-type barrier layer be provided between the semiconductor layer of the first conductivity type and the active layer and a p-type barrier layer be provided between the active layer and the semiconductor layer of the second conductivity type, respectively.

The n-type barrier layer is preferably n-type $Al_xIn_{1-x}Sb$ ($0.15 \leq x \leq 0.35$) so that the effect of the present disclosure can be improved.

The p-type barrier layer is preferably p-type $Al_xIn_{1-x}Sb$ ($0.15 \leq x \leq 0.35$) so that the effect of the present disclosure can be improved.

[Relationship Between Composition of Active Layer and Characteristics of Optical Filter]

The preferred composition of the active layer and the characteristics of the optical filter with respect to each gas to be detected are as follows.

In the case where the gas to be detected contains alcohol, it is preferable that the active layer include $InAs_ySb_{1-y}$ ($0.1 \leq y \leq 0.2$), and the optical filter include a wavelength range having an average transmittance of 70% or more and 95% or less with a width of 50 nm or more and 800 nm or less in a wavelength range of 6 μm to 10 μm and have a maximum transmittance of 10% or more in a wavelength range of 12.5 μm to 20 μm.

[Optical Device]

The optical device of the present embodiment has the same features as the NDIR gas sensor of the present embodiment described above. The optical device is not limited to a NDIR gas sensor, and may be an infrared radiation thermometer, an infrared spectral imaging, or a human body detection sensor having similar features.

According to the optical device of the present embodiment, it is possible to obtain an effect of only selectively receiving/emitting infrared light in a desired wavelength band, even using a simplified optical filter.

One aspect of the optical device of the present embodiment includes: an optical filter having a substrate and a multilayer film having a plurality of layers with different refractive indexes formed on at least one side of the substrate; and an infrared light emitting and receiving device having a semiconductor layer of a first conductive type, an active layer, and a semiconductor layer of a second conductive type; where the multilayer film has a structure in which a first layer and a second layer are alternately stacked, the first layer has a refractive index of 1.2 or more and 2.5 or less in a wavelength range of 6 μm to 10 μm, and the second layer has a refractive index of 3.2 or more and 4.3 or less in a wavelength range of 6 μm to 10 μm; the active layer contains $InAs_ySb_{1-y}$ ($0.1 \leq y \leq 0.2$); and the optical filter includes a wavelength range having an average transmittance of 70% or more and 95% or less with a width of 50 nm or more and 800 nm or less in a wavelength range of 6 μm to 10 μm and has a maximum transmittance of 10% or more in a wavelength range of 12.5 μm to 20 μm.

Another aspect of the optical device of the present embodiment includes: an optical filter having a substrate and a multilayer film having a plurality of layers with different refractive indexes formed on at least one side of the substrate; and an infrared light emitting and receiving device having a semiconductor layer of a first conductive type, an active layer, and a semiconductor layer of a second conductive type; where the multilayer film has a structure in which a first layer and a second layer are alternately stacked, the first layer contains at least one selected from the group consisting of $TiO_2$ and ZnS, and the second layer contains at least one selected from the group consisting of Si and Ge; the active layer contains $InAs_ySb_{1-y}$ ($0.1 \leq y \leq 0.2$); and the optical filter includes a wavelength range having an average transmittance of 70% or more and 95% or less with a width of 50 nm or more and 800 nm or less in a wavelength range of 6 μm to 10 μm and has a maximum transmittance of 10% or more in a wavelength range of 12.5 μm to 20 μm.

EXAMPLES

The following describes the present disclosure in detail based on Examples. However, the present disclosure is not limited to the following Examples, and may be variously modified without departing from the spirit of the disclosure.

Example 1

Figure 5:
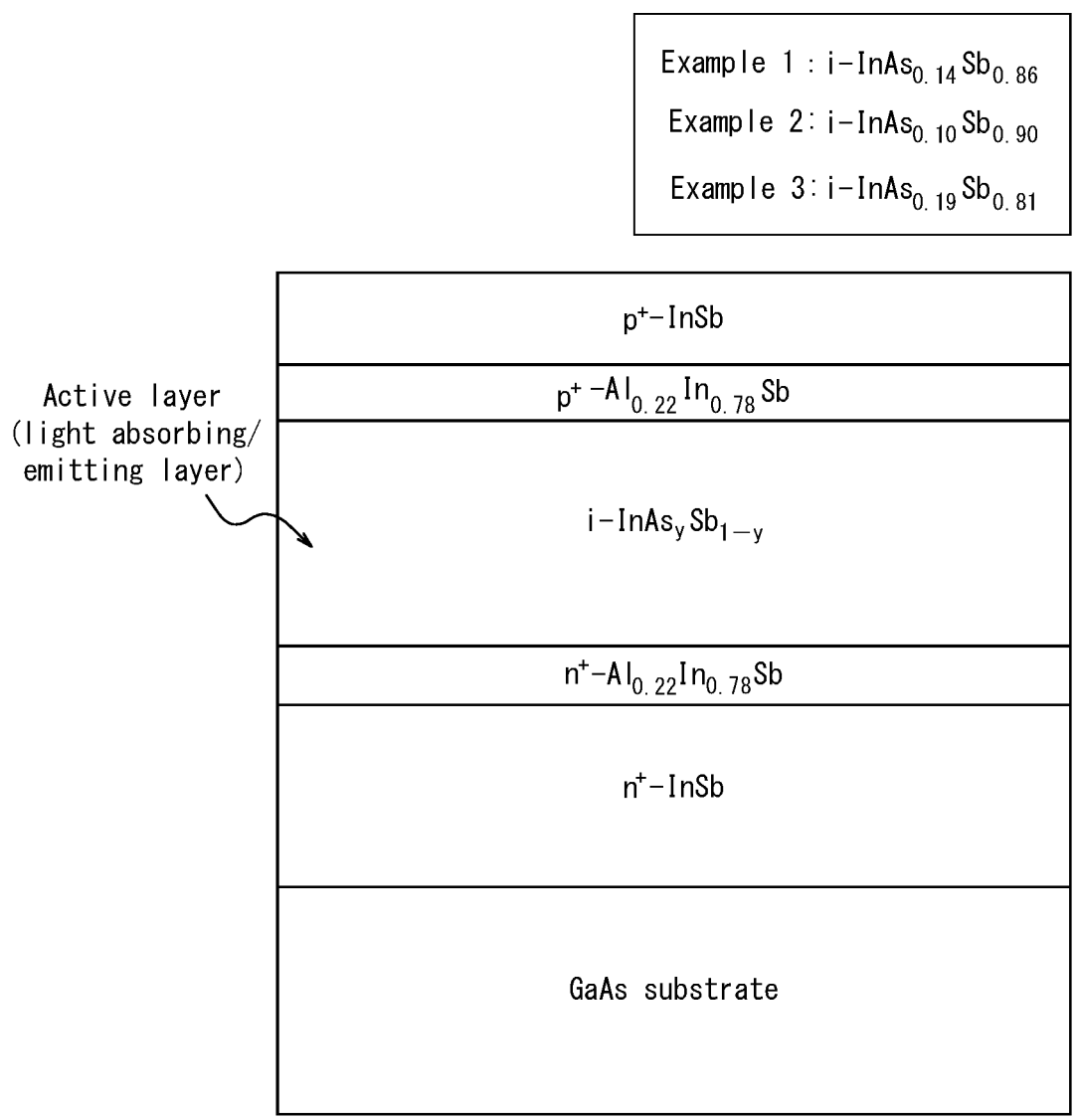
FIG. 5 illustrates the stacked structure of each layer of the infrared light emitting and receiving device of Examples 1 to 3.

The following describes an IR-sensor of Example 1 obtained by combining a simplified filter and an infrared light receiving device. The IR-sensor forms part of an optical device such as an alcohol sensor. First, a PIN diode structure was prepared with the MBE method. The active layer was $InAs_{0.4}Sb_{0.86}$. The n-type semiconductor layer was doped with Sn at $1.0 \times 10^{19}$ atoms/cm³, so that the energy band was degenerated and it was transparent to infrared light having a wavelength longer than 2 μm. In addition, n-type $Al_{0.22}In_{0.78}Sb$ and p-type $Al_{0.22}In_{0.78}Sb$ were provided as barrier layers so as to sandwich the active layer. FIG. 5 illustrates the stacked structure of each layer of the infrared light emitting and receiving device of Examples 1 to 3.

A positive photoresist for i-line was coated on the surface of the semiconductor wafer thus prepared, and exposure was performed using the i-line with a reduction projection type exposure machine. Subsequently, development was performed, and a plurality of resist patterns was regularly formed on the surface of the semiconductor stacked portion. Subsequently, a plurality of mesas was formed by dry etching. After depositing $SiO_2$ as a hard mask on the device having a mesa shape, device isolation was performed by dry etching, and then SiN was deposited as a protective film, and a contact hole was formed by photolithography and dry etching. Subsequently, a plurality of mesas was connected in series by photolithography and sputtering. Thereafter, a polyimide resin was covered on the device surface as a protective film.

Figure 6:
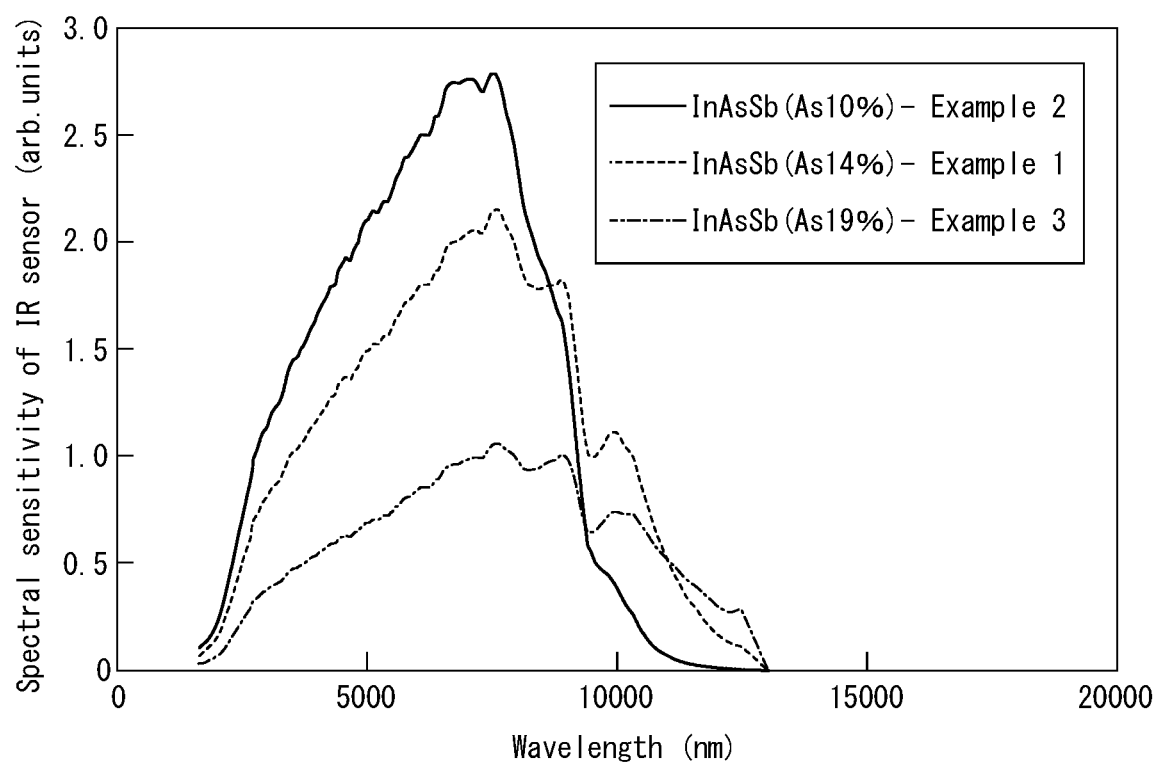
FIG. 6 illustrates the spectrum of the infrared light receiving device of Examples 1 to 3.

The wafer prepared by the above-described pre-process was diced into pieces, connected to a lead frame using Au bonding wires, and sealed with an epoxy mold resin so that a light receiving surface was exposed. The infrared light receiving device thus prepared was subjected to spectral sensitivity spectrum measurement, and the result was illustrated in FIG. 6. FIG. 6 illustrates the spectrum of the infrared light receiving device of Examples 1 to 3. This sensor is sensitive to infrared light around 9.5 μm, which is the absorption band of alcohol, but hardly sensitive to infrared light having a wavelength longer than 12.5 μm.

Figure 12:
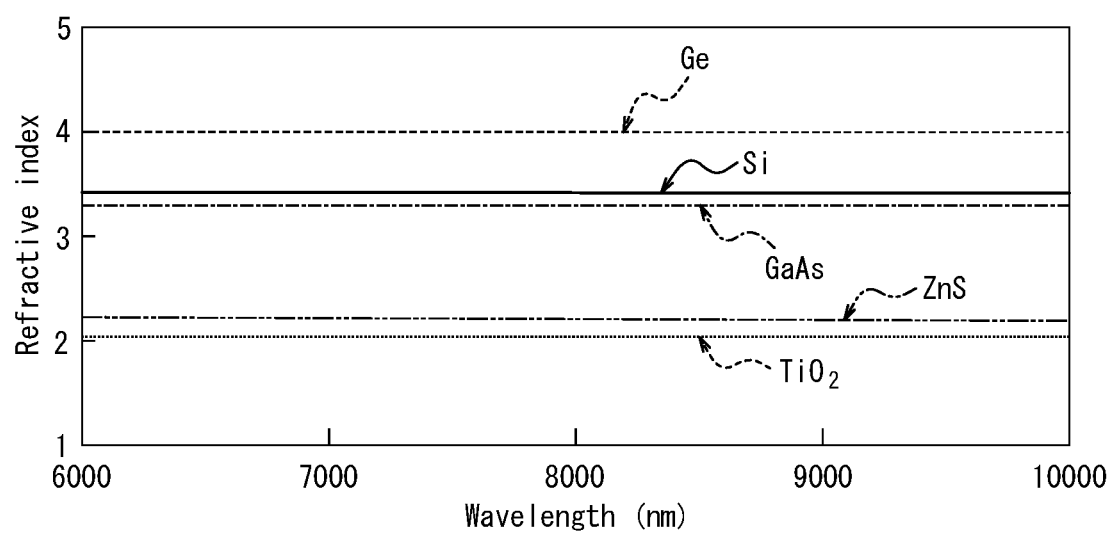
FIG. 12 illustrates the wavelength dispersion data of the refractive index of the dielectric material used for the optical filter.

The optical filter was designed based on simulation. The simulation method was a known calculation method using the Fresnel coefficient. In addition, Ge and ZnS were assumed as materials of the optical thin film, and literature values were used as the wavelength dispersion data of the complex refractive indexes. As illustrated in FIG. 12, the refractive index of Ge at 6 μm to 10 μm is about 4, and the refractive index of ZnS at 6 μm to 10 μm is about 2.2. The design of the simplified filter calculated by optical simulation is described below.

Figure 7:
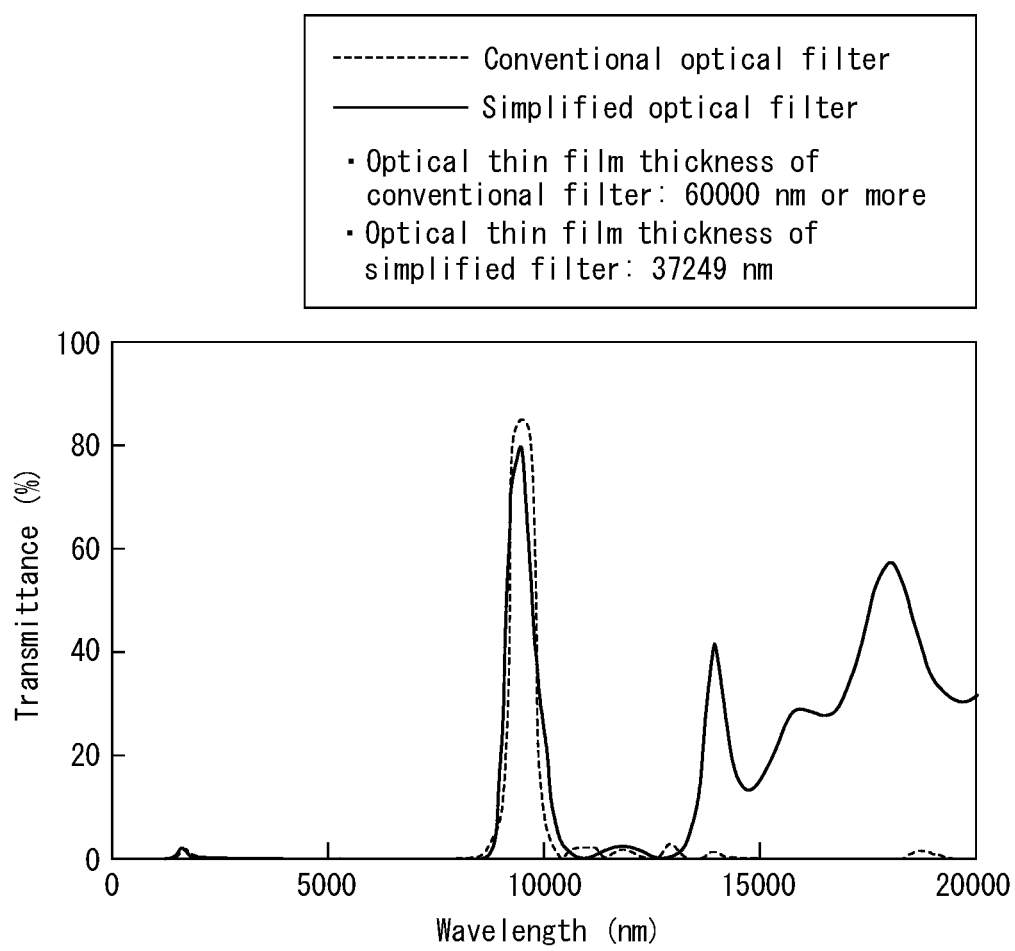
FIG. 7 illustrates and compares the transmission spectrum of the optical filter (simplified filter) of Examples 1 to 3 and the transmission spectrum of the optical filter (conventionally configured filter) of Comparative Example.

FIG. 7 illustrates and compares the transmission spectrum of the optical filter (simplified filter) of Examples 1 to 3 and the transmission spectrum of an optical filter (conventionally configured filter) of Comparative Example. FIG. 8 illustrates the stacked structure of the simplified filter of Examples 1 to 3. As illustrates in FIG. 7, the simplified filter has a transmission range of 12.5 μm or longer. Blocking function is unnecessary in this range, and thereby the thickness of the optical thin film can be reduced to 37.249 μm as compared with 60 μm of a conventional filter. The simplified filter illustrated in FIG. 7 has an average transmittance of 72% in the wavelength range of 9.3 μm to 9.7 μm. In addition, the maximum transmittance in the wavelength range of 12.5 μm to 20 μm is 57%, and the average transmittance in this wavelength range is 28%.

Figure 9:
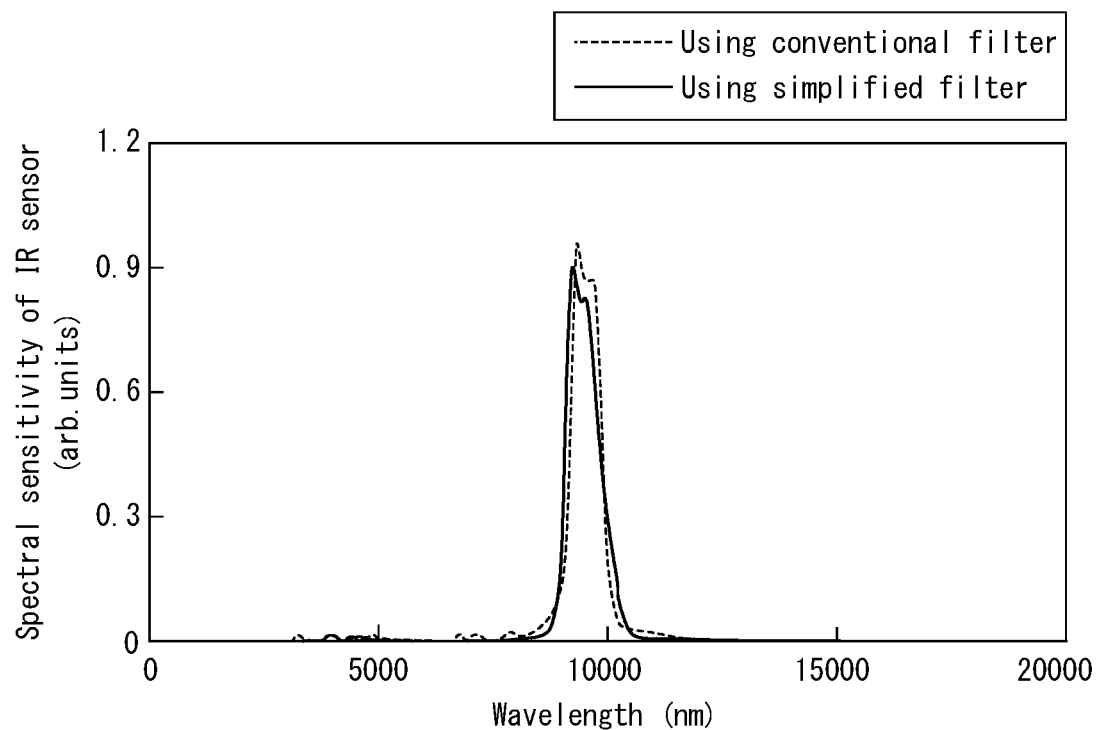
FIG. 9 illustrates the spectrum of an IR-sensor for alcohol detection which is configured by combining the infrared light receiving device and the optical filter (simplified filter) of Example 1.

Next, FIG. 9 illustrates the spectrum of an IR-sensor for alcohol detection which is configured by combining the infrared light receiving device and the optical filter (simplified filter) of Example 1. As the result indicates, the output when combined with the infrared light receiving device is equivalent regardless of which optical filter is used. In other words, it is indicated that the design of the optical filter can be greatly simplified without any deterioration in the performance as a sensor component for a NDIR type gas sensor.

Example 2

Figure 10:
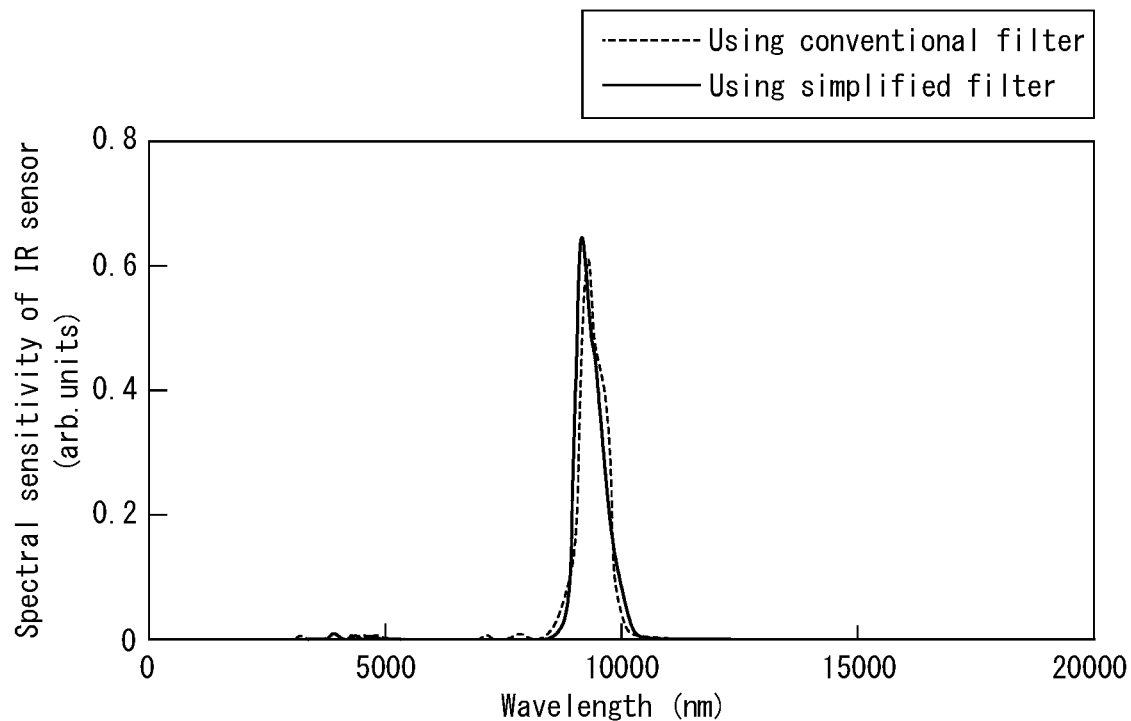
FIG. 10 illustrates the spectrum of an IR-sensor for alcohol detection which is configured by combining the infrared light receiving device and the optical filter (simplified filter) of Example 2.

Example 2 is the same as Example 1 except that the active layer was $InAs_{0.1}Sb_{0.90}$. FIG. 10 illustrates the spectrum of an IR-sensor for alcohol detection which is configured by combining the infrared light receiving device and the optical filter (simplified filter) of Example 2. As the result indicates, the output when combined with the infrared light receiving device is equivalent regardless of which optical filter is used. In other words, it is indicated that the design of the optical filter can be greatly simplified without any deterioration in the performance as a sensor component for a NDIR type gas sensor.

Example 3

Figure 11:
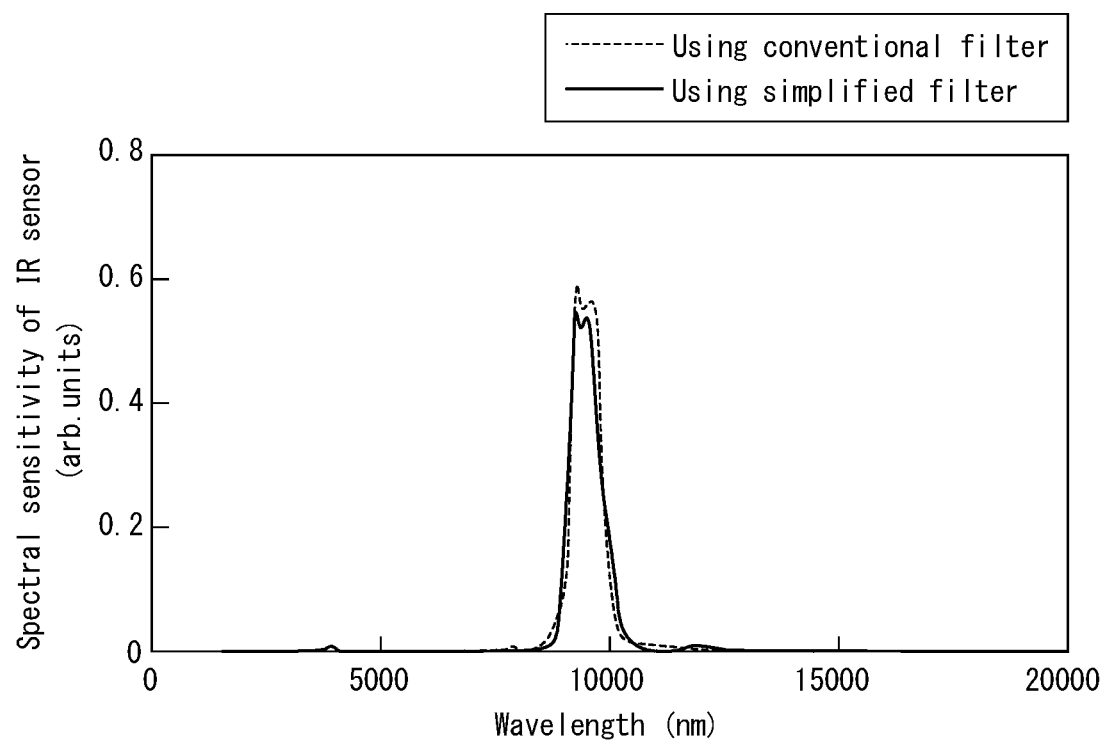
FIG. 11 illustrates the spectrum of an IR-sensor for alcohol detection which is configured by combining the infrared light receiving device and the optical filter (simplified filter) of Example 3.

Example 3 is the same as Example 1 except that the active layer was $InAs_{0.19}Sb_{0.81}$. FIG. 11 illustrates the spectrum of an IR-sensor for alcohol detection which is configured by combining the infrared light receiving device and the optical filter (simplified filter) of Example 3. As the result indicates, the output when combined with the infrared light receiving device is equivalent regardless of which optical filter is used. In other words, it is indicated that the design of the optical filter can be greatly simplified without any deterioration in the performance as a sensor component for a NDIR type gas sensor.

The wavelength dispersion data of the refractive index of the dielectric material used in the optical simulation of Examples 1 to 3 are illustrated in FIG. 12.

Detailed conditions and results of Examples and Comparative Example are listed in Table 1. The wavelength-transmittance curves of Examples 1 to 3 and Comparative Example are illustrated in FIG. 7

TABLE 1

| | | | | | Example 1 | Example 2 | Example 3 | Comparative Example |
|---|---|---|---|---|---|---|---|---|
| Optical filter | Multilayer film | Substrate | | | Si | Si | Si | Si |
| | | Film configuration | First layer | Material | ZnS | ZnS | ZnS | ZnS |
| | | | Second layer | Material | Ge | Ge | Ge | Ge |
| | | Number of repeating units | | | 44.5 | 44.5 | 44.5 | 50 or more |
| | | Film thickness | | | 37249 nm | 37249 nm | 37249 nm | >60000 nm |
| | | Wavelength range where the average transmittance is 70 % or more from 6000 nm to 10000 nm | | | 9300 nm to 9700 nm has an average transmittance of 72% | 9300 nm to 9700 nm has an average transmittance of 72% | 9300 nm to 9700 nm has an average transmittance of 72% | 9300 nm to 9700 nm has an average transmittance of 81% |
| | | Maximum transmittance at 12500 nm to 20000 nm | | | Maximum transmittance at 12500 nm to | Maximum transmittance at 12500 nm to | Maximum transmittance at 12500 nm to | Maximum transmittance at 12500 nm to 20000 nm |
| | | Average transmittance at 12500 nm to 20000 nm | | | | | | |

TABLE 1-continued

|  |  |  | Example 1 | Example 2 | Example 3 | Comparative Example |
|---|---|---|---|---|---|---|
|  |  |  | 20000 nm is 57% Average transmittance at 12500 nm to 20000 nm is 28% | 20000 nm is 57% Average transmittance at 12500 nm to 20000 nm is 28% | 20000 nm is 57% Average transmittance at 12500 nm to 20000 nm is 28% | is 3% or less Average transmittance at 12500 nm to 20000 nm is 0.3% |
| Infrared light emitting and receiving device | Semiconductor layer of first conductive type | n-type | InSb | InSb | InSb | InSb |
|  | Semiconductor layer of first conductive type | n-type | InSb | InSb | InSb | InSb |
|  | Barrier layer | n-type | $Al_{0.22}In_{0.78}Sb$ | $Al_{0.22}In_{0.78}Sb$ | $Al_{0.22}In_{0.78}Sb$ | None |
|  | Active layer | i-type | $InAs_{0.14}Sb_{0.86}$ | $InAs_{0.10}Sb_{0.90}$ | $InAs_{0.19}Sb_{0.81}$ | InSb |
|  | Barrier layer | p-type | $Al_{0.22}In_{0.78}Sb$ | $Al_{0.22}In_{0.78}Sb$ | $Al_{0.22}In_{0.78}Sb$ | $Al_{0.22}In_{0.78}Sb$ |
|  | Semiconductor layer of second conductive type | p-type | InSb | InSb | InSb | InSb |

According to Table 1, although Examples 1 to 3 have an optical filter where the film thickness is 63% or less of that of Comparative Example, they can provide equivalent performance when combined with the infrared light emitting and receiving device. Comparative Example is different from Examples 1 to 3 in that the maximum transmittance in the wavelength range of 12.5 μm to 20 μm is 3% or less, which is less than 10%. In addition, Comparative Example is different from Examples 1 to 3 in that the average transmittance in the wavelength range of 12.5 μm to 20 μm is 0.3%, which is less than 5%.

According to the present disclosure, it is possible to provide a NDIR gas sensor with high accuracy even using a simplified optical filter, an optical device, and an optical filter for a NDIR gas sensor.

In addition, the infrared light emitting device of Example 2, the infrared light receiving device of any of Examples 1 to 3, and the simplified filter may be combined to constitute an optical device.

One including an optical filter having a band having an average transmittance of 70% or more with a width of 50 nm or more in a wavelength range of 9 μm to 10 μm is a sub-combination of the above embodiment and is included in the present disclosure. In this case, the multilayer film has a structure in which a first layer and a second layer are alternately stacked, the first layer has a refractive index of 1.2 or more and 2.5 or less in a wavelength range of 9 μm to 10 μm, and the second layer has a refractive index of 3.2 or more and 4.3 or less in a wavelength range of 9 μm to 10 μm. In addition, one including an optical filter having a band having an average transmittance of 70% or more with a width of 50 nm or more in a wavelength range of 7 μm to 11 μm is also included in the present disclosure. In this case, the multilayer film has a structure in which a first layer and a second layer are alternately stacked, the first layer has a refractive index of 1.2 or more and 2.5 or less in a wavelength range of 7 μm to 11 μm, and the second layer has a refractive index of 3.2 or more and 4.3 or less in a wavelength range of 7 μm to 11 μm.

The invention claimed is:

1. An optical device comprising:
   an optical filter having a substrate and a multilayer film having a plurality of layers with different refractive indexes formed on at least one side of the substrate; and
   an infrared light emitting and receiving device having a semiconductor layer of a first conductive type, an active layer, and a semiconductor layer of a second conductive type; wherein
   the multilayer film has a structure in which a first layer and a second layer are alternately stacked, the first layer has a refractive index of 1.2 or more and 2.5 or less in a wavelength range of 6 μm to 10 μm, and the second layer has a refractive index of 3.2 or more and 4.3 or less in a wavelength range of 6 μm to 10 μm; and
   the optical filter includes a wavelength range having an average transmittance of 70% or more with a width of 50 nm or more in a wavelength range of 6 μm to 10 μm, and has a maximum transmittance of 10% or more in a wavelength range of 12.5 μm to 20 μm.

2. The optical device according to claim 1, wherein the active layer contains In, As, and Sb.

3. The optical device according to claim 1, wherein the optical device has no sensitivity or does not emit light, in a wavelength range of 12.5 μm to 20 μm.

4. The optical device according to claim 1, wherein the optical filter has an average transmittance of 5% or more in a wavelength range of 12.5 μm to 20 μm.

5. The optical device according to claim 1, wherein the active layer contains $InAs_ySb_{1-y}$ (0.1≤y≤0.2); and
   the optical filter includes a wavelength range having an average transmittance of 70% or more and 95% or less with a width of 50 nm or more and 800 nm or less in a wavelength range of 9 μm to 10 μm, and has a maximum transmittance of 10% or more in a wavelength range of 12.5 μm to 20 μm.

6. The optical device according to claim 5, wherein a gas to be detected is alcohol.

7. The optical device according to claim 1, wherein a film thickness of the multilayer film is 10 μm or more and 50 μm or less.

8. The optical device according to claim 1, wherein the number of times the first layer and the second layer are alternately stacked in the multilayer film is 10 or more and 60 or less.

9. The optical device according to claim 1, wherein the first layer contains at least one selected from the group consisting of $TiO_2$ and ZnS.

10. The optical device according to claim 1, wherein the second layer contains at least one selected from the group consisting of Si and Ge.

11. The optical device according to claim 1, wherein the infrared light emitting and receiving device is an infrared LED or an infrared photodiode or both.

12. The optical device according to claim 1, wherein the infrared light emitting and receiving device is an infrared LED and an infrared photodiode.

13. The optical device according to claim 1, wherein the multilayer film is formed on both sides of the substrate.

14. An optical device comprising
an optical filter having a substrate and a multilayer film having a plurality of layers with different refractive indexes formed on at least one side of the substrate; and
an infrared light emitting and receiving device having a semiconductor layer of a first conductive type, an active layer, and a semiconductor layer of a second conductive type; wherein
the multilayer film has a structure in which a first layer and a second layer are alternately stacked, the first layer contains at least one selected from the group consisting of $TiO_2$ and ZnS, and the second layer contains at least one selected from the group consisting of Si and Ge; and
the optical filter includes a wavelength range having an average transmittance of 70% or more with a width of 50 nm or more in a wavelength range of 6 μm to 10 μm, and has a maximum transmittance of 10% or more in a wavelength range of 12.5 μm to 20 μm.

\* \* \* \* \*